(12) United States Patent
Oishi et al.

(10) Patent No.: US 8,689,609 B2
(45) Date of Patent: Apr. 8, 2014

(54) HYDROGEN SENSOR WITH DEW CONDENSATION PREVENTION

(75) Inventors: Hidetoshi Oishi, Utsunomiya (JP);
Akihiro Suzuki, Utsunomiya (JP);
Shunji Tsukabayashi, Shioya-gun (JP);
Kazuhiro Okajima, Yuki (JP)

(73) Assignee: Honda Motor Co., Ltd., Tokyo (JP)

( * ) Notice: Subject to any disclaimer, the term of this patent is extended or adjusted under 35 U.S.C. 154(b) by 612 days.

(21) Appl. No.: 12/937,646

(22) PCT Filed: Apr. 15, 2009

(86) PCT No.: PCT/JP2009/057612
§ 371 (c)(1),
(2), (4) Date: Oct. 13, 2010

(87) PCT Pub. No.: WO2009/128484
PCT Pub. Date: Oct. 22, 2009

(65) Prior Publication Data
US 2011/0023580 A1 Feb. 3, 2011

(30) Foreign Application Priority Data
Apr. 15, 2008 (JP) .................................. 2008-105780

(51) Int. Cl.
*G01N 25/18* (2006.01)

(52) U.S. Cl.
USPC ........................................ 73/25.05; 73/25.03

(58) Field of Classification Search
USPC .......................... 73/23.2, 23.21, 25.03, 25.05
See application file for complete search history.

(56) References Cited

U.S. PATENT DOCUMENTS

| | | | | |
|---|---|---|---|---|
| 4,184,934 A | * | 1/1980 | Bode et al. | ..................... 204/428 |
| 4,861,557 A | * | 8/1989 | McNally | .......................... 422/97 |
| 5,057,436 A | * | 10/1991 | Ball | .............................. 436/113 |
| 5,599,584 A | | 2/1997 | Champney, Jr. | |

(Continued)

FOREIGN PATENT DOCUMENTS

| | | |
|---|---|---|
| EP | 1452853 A1 | 9/2004 |
| JP | 9-33473 | 2/1997 |
| JP | 10-10067 | 1/1998 |
| JP | 4024210 B2 | 10/2007 |

OTHER PUBLICATIONS

Supplementary European Search Report for Application No. 09733410.6, 3 pages, dated Oct. 15, 2012.

*Primary Examiner* — Lisa Caputo
*Assistant Examiner* — Punam Roy
(74) *Attorney, Agent, or Firm* — Nelson Mullins Riley & Scarborough LLP; Anthony A. Laurentano

(57) ABSTRACT

The gas sensor includes: a cylindrical member which includes a gas detection chamber therein and extends along an axial thereof; a base member which closes an opening of a first axial end of the cylindrical member; a status sensor which is disposed at a substantially central portion of the base member, and detects at least the temperature or the humidity in the gas detection chamber; a gas detection element disposed around the status sensor on the base member; a lid member which closes an opening of a second axial end of the cylindrical member; and a gas inlet port which penetrates the lid member at a location not coinciding with the status sensor and the gas detection element when seen from the axial direction, and enables the introduction of an inspection target gas from an outside into the gas detection chamber.

6 Claims, 7 Drawing Sheets

(56) References Cited

U.S. PATENT DOCUMENTS

| | | | |
|---|---|---|---|
| 5,879,631 A * | 3/1999 | Wewers et al. | 422/98 |
| 6,322,247 B1 * | 11/2001 | Bonne et al. | 374/138 |
| 6,344,174 B1 * | 2/2002 | Miller et al. | 422/98 |
| 6,849,238 B2 * | 2/2005 | Weyl et al. | 422/94 |
| 7,021,821 B2 * | 4/2006 | Bonne | 374/44 |
| 7,104,110 B2 * | 9/2006 | Oishi et al. | 73/1.06 |
| 7,251,981 B2 * | 8/2007 | Sasaki et al. | 73/23.21 |
| 7,269,993 B2 * | 9/2007 | Oishi et al. | 73/23.31 |
| 7,342,505 B2 * | 3/2008 | Sasaki et al. | 340/632 |
| 7,360,395 B2 * | 4/2008 | Sasaki et al. | 73/25.05 |
| 7,418,855 B2 * | 9/2008 | Oishi et al. | 73/25.03 |
| 7,479,255 B2 * | 1/2009 | Otani et al. | 422/94 |
| 7,537,737 B2 * | 5/2009 | Abe et al. | 422/606 |
| 7,568,375 B2 * | 8/2009 | Sasaki et al. | 73/23.2 |
| 7,827,847 B2 * | 11/2010 | Oishi et al. | 73/23.2 |
| 2003/0190261 A1 * | 10/2003 | Abe et al. | 422/94 |
| 2005/0042141 A1 * | 2/2005 | Otani et al. | 422/98 |
| 2005/0061055 A1 * | 3/2005 | Oishi et al. | 73/23.2 |
| 2005/0072212 A1 * | 4/2005 | Oishi et al. | 73/23.21 |
| 2005/0155405 A1 * | 7/2005 | Sasaki et al. | 73/1.06 |
| 2005/0284208 A1 * | 12/2005 | Oishi et al. | 73/23.2 |
| 2006/0042965 A1 * | 3/2006 | Sasaki et al. | 205/784 |
| 2006/0048562 A1 * | 3/2006 | Oishi et al. | 73/23.2 |
| 2006/0113198 A1 * | 6/2006 | Sasaki et al. | 205/775 |
| 2006/0113199 A1 * | 6/2006 | Sasaki et al. | 205/783 |
| 2006/0219552 A1 * | 10/2006 | Sasaki et al. | 204/424 |
| 2006/0269806 A1 * | 11/2006 | Suzuki et al. | 429/22 |
| 2007/0026275 A1 | 2/2007 | Sasaki et al. | |
| 2007/0028666 A1 * | 2/2007 | Sasaki et al. | 73/23.21 |
| 2008/0092628 A1 * | 4/2008 | Oishi et al. | 73/25.01 |
| 2008/0175759 A1 * | 7/2008 | Oishi et al. | 422/98 |
| 2008/0219895 A1 * | 9/2008 | Sasaki et al. | 422/83 |
| 2010/0139389 A1 * | 6/2010 | Morita et al. | 73/204.11 |

* cited by examiner

HYDROGEN SENSOR WITH DEW CONDENSATION PREVENTION

RELATED APPLICATIONS

This application is a 35 U.S.C. 371 national stage filing of International Application No. PCT/JP2009/057612, filed Apr. 15, 2009, which claims priority to Japanese Patent Application No. 2008-105780 filed on Apr. 15, 2008 in Japan. The contents of the aforementioned applications are hereby incorporated by reference.

TECHNICAL FIELD

The present invention relates to a gas sensor.
Priority is claimed on Japanese Patent Application No. 2008-105780, filed Apr. 15, 2008, the content of which is incorporated herein by reference.

BACKGROUND ART

A known related art gas sensor is provided with a gas inlet port for the introduction of an inspection target gas into a gas detection chamber constituted by a case in which a gas detection element is installed (for example, see Japanese Patent No. 4024210).

DISCLOSURE OF THE INVENTION

Problems to be Solved by the Invention

For the related art gas sensor described above, there is no clear explanation about a relationship between locations of the gas detection element and each of sensors for detecting the temperature or the like in the gas detection chamber disposed in the gas detection chamber, in relation to a location of the gas inlet port of the case. This means that, for example, the gas detection element or each of the sensors may be disposed on a path through which the inspection target gas introduced into the gas detection chamber from the gas inlet port of the case flows when a predetermined gas included in the inspection target gas is to be detected in a high temperature and high humidity environment. In this case, the inspection target gas of a high humidity and a high moisture content may come into direct contact with the gas detection element or each of the sensors, which easily causes dew condensation. When, for example, electrical power is supplied to the gas detection element or each of the sensors on which dew condensation occurs, problems of the destruction of the detection element or the reduction in sensitivity may be caused.

The present invention was made in view of the above-mentioned circumstances, and an object thereof is to provide a gas sensor that can prevent the occurrence of problems due to dew condensation.

Means for Solving the Problems

First Aspect

A gas sensor related to a first aspect of the present invention employs the following configuration: a gas sensor, which includes: a cylindrical member which includes a gas detection chamber therein and extends along an axis thereof; a base member which closes an opening of a first axial end of the cylindrical member; a status sensor which is disposed at a substantially central portion of the base member, and detects at least the temperature or the humidity in the gas detection chamber; a gas detection element disposed around the status sensor on the base member; a lid member which closes an opening of a second axial end of the cylindrical member; and a gas inlet port which penetrates the lid member at a location not coinciding with the status sensor and the gas detection element when seen from the axial direction, and enables the introduction of an inspection target gas from an outside into the gas detection chamber.

Second Aspect

The above-described gas sensor may be configured as follows: a plurality of the gas detection elements are arranged on a first circumference; and a plurality of the gas inlet ports are arranged on a second circumference of a larger diameter than that of the first circumference.

Third Aspect

The above-described gas sensor may be configured as follows: the gas sensor further includes an annular water-repellent filter which covers all the plurality of the gas inlet ports arranged on the second circumference.

Fourth Aspect

The above-described gas sensor may be configured as follows: the gas sensor further includes: a heater disposed on a wall of the cylindrical member or on the lid member to heat the inside of the gas detection chamber; and an explosion-proof filter which covers the plurality of the gas inlet ports, and is made from metal, in which a heat-transfer structure is provided which transfers heat generated by the heater to the explosion-proof filter.

Fifth Aspect

The above-described gas sensor may be configured as follows: the heater is disposed on the wall of the cylindrical member; the explosion-proof filter has an annular shape to cover all the plurality of the gas inlet ports arranged on the second circumference; and the heat-transfer structure transfers heat generated by the heater from radially outside toward the inside of the explosion-proof filter.

Sixth Aspect

The above-described gas sensor may be configured as follows: the plurality of the gas detection elements are arranged on a first circumference; the plurality of the gas inlet ports are arranged on the first circumference or on a second circumference of a different diameter from that of the first circumference; and the plurality of the gas detection elements arranged on the first circumference and the plurality of the gas inlet ports arranged on the first circumference or the second circumference are positioned in different phases along the circumferential direction.

Effect of the Invention

As described above, according to the gas sensor related to the first aspect of the present invention, the gas inlet ports which allow the introduction of the inspection target gas from outside into the gas detection chamber are arranged not coinciding with and not in alignment with the status sensor and the gas detection elements in the gas detection chamber when seen from the axial direction. Accordingly, the status sensor and the gas detection elements are arranged at locations off a path through which the inspection target gas flows. It is therefore possible to prevent the flow of the inspection target gas from blown directly against the status sensor and the gas detection elements. In addition, even if the inspection target gas has a high moisture content and a high humidity, the occurrence of dew condensation in the status sensor and the gas detection elements can be prevented. Since the status sensor is disposed at the substantially central portion of the base member, accuracy and reliability in detection of the temperature or the humidity within the gas detection chamber can be improved.

According to the gas sensor related to the second aspect of the present invention, the plurality of the gas detection elements can be arranged more densely in a case in which the plurality of the gas detection elements are arranged not coinciding with and not in alignment with the gas inlet ports when seen from the axial direction. Thus, the size of the gas sensor can be reduced.

According to the gas sensor related to the third aspect of the present invention, all the plurality of the gas inlet ports arranged on the second circumference can be covered with a single annular water-repellent filter. It is therefore possible to keep the water-repellent filter simply-structured and compact, and to prevent an increase in the number of the water-repellent filters.

According to the gas sensor related to the fourth aspect of the present invention, a heat-transfer structure for transferring heat generated by the heater to the explosion-proof filter is a structure in which the heater and the explosion-proof filter are in direct contact with each other, or, for example, a highly heat conductive heat-transfer member is provided to connect the heat and the explosion-proof filter. Accordingly, the explosion-proof filter can be efficiently heated by the heat transferred from the heater, and clogging of the explosion-proof filter due to dew condensation can be prevented.

According to the gas sensor related to the fifth aspect of the present invention, all the plurality of the gas inlet ports arranged on the second circumference can be covered with a single annular explosion-proof filter. It is therefore possible to keep the explosion-proof filter simply-structured and compact, and to prevent an increase in number of the explosion-proof filter. In particular, for example, the radially outside portion of the explosion-proof filter may be in direct contact with the heater, or a highly heat conductive heat-transfer member may be provided to connect the heater and the radially outside portion of the explosion-proof filter. Accordingly, in the annular explosion-proof filter, the heat generated by the heater is transferred from the radially outside portion with a relatively large heat releasing area toward the inside with a relatively small heat releasing area. Thus the explosion-proof filter can be heated efficiently.

According to the gas sensor related to the sixth aspect of the present invention, the plurality of the gas detection elements arranged on the first circumference and the plurality of the gas inlet ports arranged on the first circumference or a predetermined circumference are positioned in different phases. Accordingly, the plurality of the gas detection elements and the plurality of the gas inlets ports can be arranged more densely, which reduces the size of the gas sensor.

EMBODIMENTS OF THE INVENTION

A gas sensor according to one embodiment of the present invention will be described below with reference to the accompanying drawings.

Figure 1:
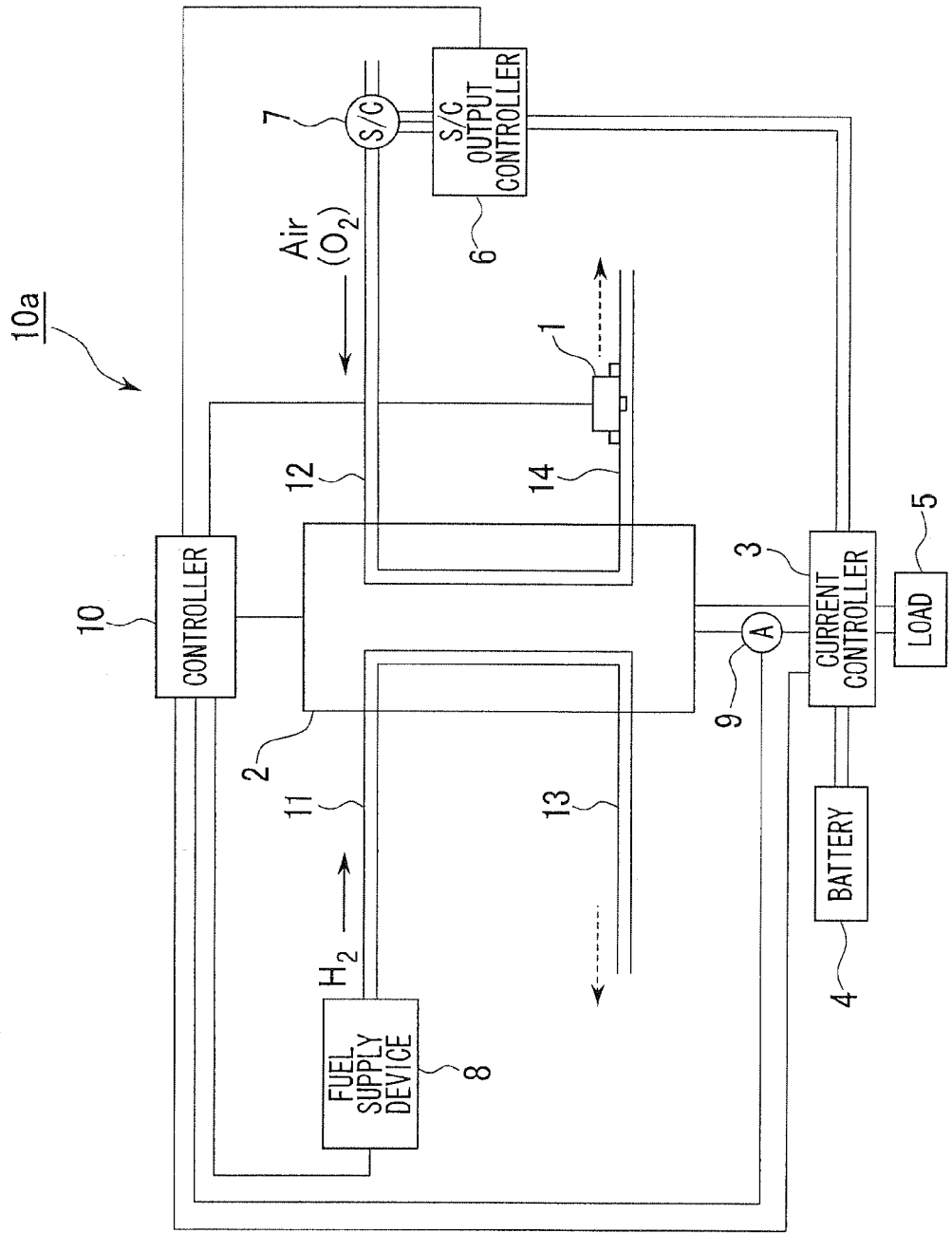
FIG. 1 is a configuration diagram of a fuel cell system equipped with a gas sensor according to one embodiment of the present invention.

As shown in, for example FIG. 1, a gas sensor 1 according to the present embodiment is installed in a fuel cell system 10a. The fuel cell system 10a is provided with a fuel cell stack 2, a current controller 3, a battery 4, a load 5, an S/C output controller 6, a supercharger (S/C) 7, a fuel supply device 8, an output current sensor 9 and a controller 10. Among lines 11, 12, 13 and 14 which are connected to the fuel cell stack 2, the gas sensor 1 is provided at the outlet line 14 on an oxygen electrode side.

The fuel cell stack 2 is mounted as a driving source in a vehicle such as an electric vehicle. The fuel cell stack 2 is constituted by a plurality of fuel cells (not illustrated), each fuel cell consisting of an electrolyte electrode structure sandwiched by a pair of separators. The electrolyte electrode structure consists of a solid polymer electrolyte membrane which is held between a hydrogen electrode and an oxygen electrode.

A fuel gas containing hydrogen is supplied from the fuel supply device 8 having a high-pressure hydrogen tank and the like, to the inlet line 11 that is connected to the hydrogen electrode of the fuel cell stack 2. Hydrogen that is ionized at a catalyst electrode of the hydrogen electrode moves to the oxygen electrode through the solid polymer electrolyte membrane which is properly humidified. Electrons that are generated as a result of the movement of hydrogen are taken out to an outer circuit, and used as direct current energy.

An oxidizing gas such as oxygen or air is supplied from the super charger (S/C) 7 to the inlet line 12 that is connected to the oxygen electrode. Water is generated at the oxygen electrode as a result of a reaction of hydrogen ions, electrons, and oxygen. A gas remaining after the reaction, also called "off-gas," is discharged through the outlet lines 13 and 14 from the hydrogen electrode and the oxygen electrode respectively. Especially, since a solid polymer electrolyte type fuel cell usually has an operating temperature that is lower than a vaporization temperature of water, the off-gas is discharged as a gas with a high humidity and a high moisture content.

The gas sensor 1, which is a gas-contact combustion-type sensor, is provided vertically above the outlet line 14 on the oxygen electrode side. The gas sensor 1 enables confirmation that the hydrogen gas is not discharged through the outlet line 14 on the oxygen electrode side.

The supercharger (S/C) 7 takes air in, for example, from outside of the vehicle and compresses the same, and supplies the compressed air as a reaction gas to the oxygen electrode side of the fuel cell stack 2.

The rotational speed of a motor (not illustrated) that drives the supercharger (S/C) 7 is controlled by the S/C output controller 6 having, for example, a PWM inverter that performs pulse wave modulation (PWM), in accordance with a control instruction input from the controller 10.

The generated current (the output current) extracted from the fuel cell stack 2 is input to the current controller 3. The current controller 3 is connected to the battery 4 having a capacitor that is formed by tandemly connecting a plurality of capacitor cells each formed from, for example, an electric double layer condenser and an electrolytic condenser.

The fuel cell stack 2, the current controller 3 and the battery 4 are connected to the load 5 and the S/C output controller 6, in a parallel manner. The load 5 includes, for example, a traction motor (not illustrated) and auxiliary equipment such as a cooler (not illustrated) and an air conditioner (not illustrated) for, for example, the fuel cell stack 2 and the battery 4.

In the fuel cell system 10a, the controller 10 operates in accordance with, for example, the driving state of the vehicle, the hydrogen concentration in the fuel gas supplied to the hydrogen electrode of the fuel cell stack 2, the hydrogen concentration in the off-gas discharged from the hydrogen electrode of the fuel cell stack 2, and the power generating state of the fuel cell stack 2 (for example, the voltage between terminals of the plurality of the fuel cells and the output current extracted from the fuel cell stack 2). The controller 10 outputs instruction values for the flow rates of the air supplied from the supercharger (S/C) 7 to the fuel cell stack 2, and for the flow rate of the fuel gas supplied from the fuel supply device 8 to the fuel cell stack 2. In this manner, the controller 10 controls the power generating state of the fuel cell stack 2.

Detection signals output from the output current sensor 9, which detects the current value of the output current extracted from the fuel cell stack 2, are input to the controller 10.

The controller 10 controls the value of the output current extracted from the fuel cell stack 2 by the current controller 3 in accordance with power generation instruction (i.e., the FC output instruction value) to the fuel cell stack 2.

Figure 2:
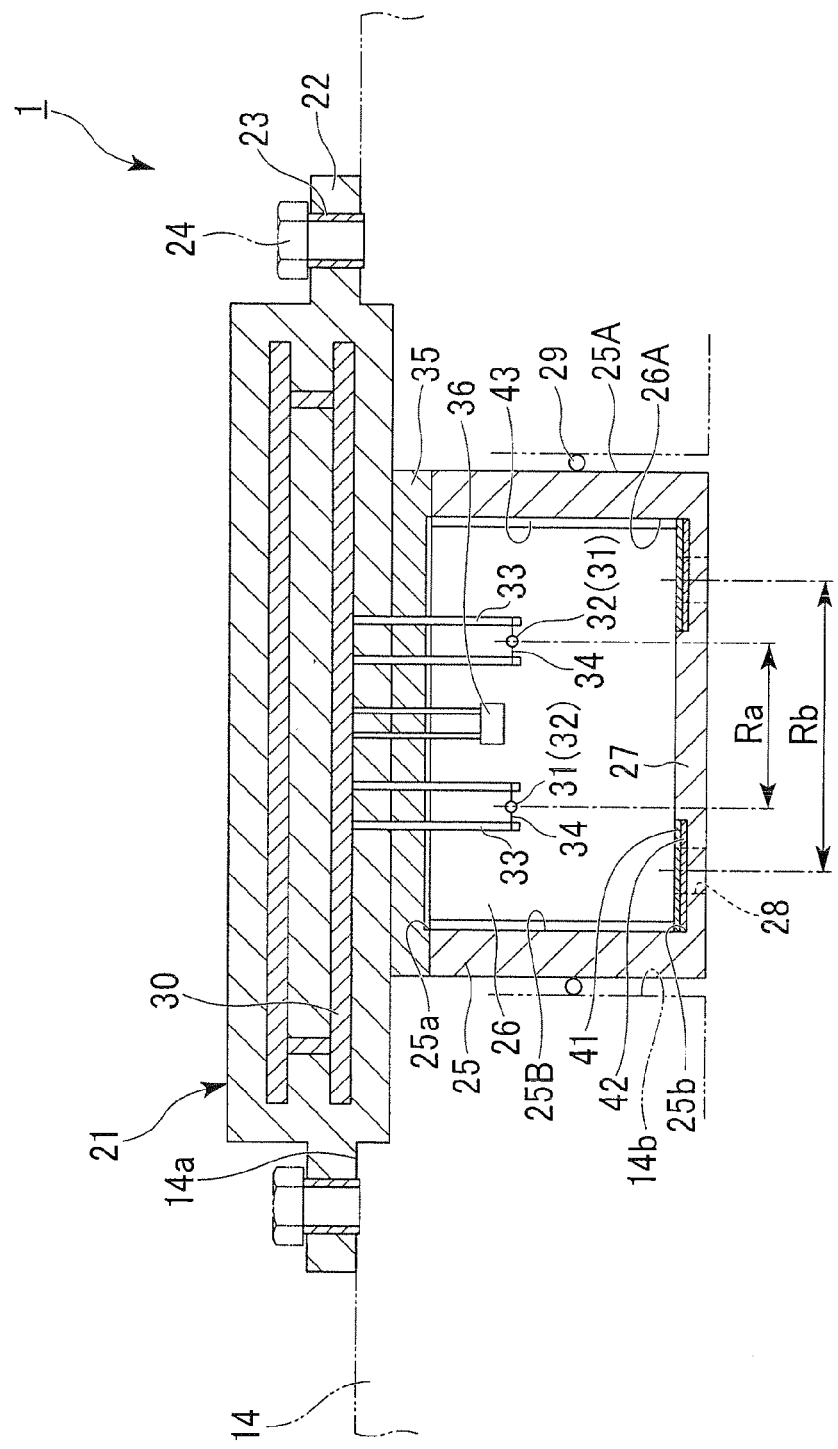
FIG. 2 is a side sectional view of a gas sensor according to one embodiment of the present invention.

As shown in for example FIG. 2, the gas sensor 1 is provided with a rectangular shaped case 21 that extends along the length of the outlet line 14. The case 21 is made from, for example, polyphenylene sulfide. The case 21 has flange portions 22 on the both sides in the length thereof. Each of the flange portions 22 has a collar 23 and is fixed to a mounting seat 14a of the outlet line 14 by screwing bolts 24 inserted in the collars 23.

A ceramic-made cylinder member 25 is provided on one end surface (for example, a lower end surface) of the case 21 in the thickness thereof, via a base member 35. The cylinder member 25 is inserted from the exterior of the outlet line 14 into a penetration hole formed in the outlet line 14.

The inside of the cylinder member 25 is formed as a gas detection chamber 26. An opening 25a of the cylinder member 25 in one end (for example, an upper end) in the axial direction (for example, the vertical direction) is closed by the base member 35.

An opening 25b of the cylinder member 25 in the other end (for example, a lower end) in the axial direction is covered with, for example, a ceramic-made lid-shaped member (lid member) 27. The lid-shaped member 27 is provided with a plurality of (for example, four) gas inlet ports 28 that penetrate the lid-shaped member 27 in the axial direction.

Figure 3:
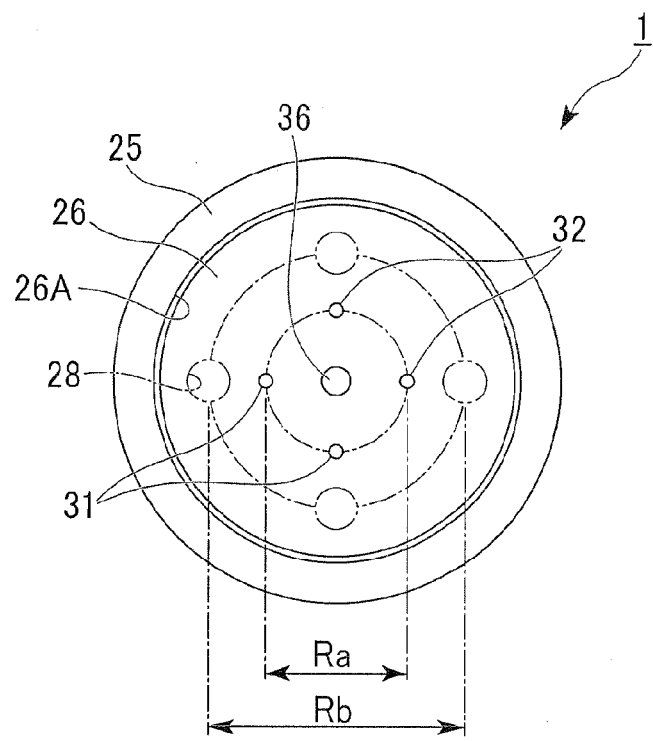
FIG. 3 is an axial sectional view of a gas sensor according to a variant example of one embodiment of the present invention.

As illustrated for example in FIG. 3, the plurality of (for example, four) gas inlet ports 28 are arranged at a predetermined interval on a second circumference which is located at a predetermined second diameter Rb from the center of the lid-shaped member 27.

As illustrated for example in FIG. 2, a sealing member 29 is attached onto an external surface 25A of the cylinder member 25, and comes into fitting contact with the inner wall of the penetration hole 14b in the outlet line 14 to secure the airtightness.

A circuit board 30 sealed with a resin material is provided in the case 21. For example, two pairs of a detection element 31 and a temperature compensation element 32 disposed in the gas detection chamber 26 are connected to the circuit board 30 via a plurality of stays 33 (i.e., supporting members) and lead wires 34 provided as electrical paths.

The stays 33 are formed as electrical paths, for example, from compound alloy materials, such as copper alloy, ferrous alloy and nickel alloy. The stays 33 penetrate the substantially ring plate-shaped base member 35 arranged between the case 21 and the cylinder member 25. The bottom ends of the stays 33 are connected to the circuit board 30 in the case 21, while the distal ends of the stays 33 are fixed to the base member 35 so as to protrude into the gas detection chamber 26. The base member 35 is a plate member formed from an insulation material such as alumina or glass epoxy.

A status sensor 36 is disposed at a substantially central portion of the base member 35 to detect the temperature and the humidity near the elements 31 and 32 within the gas detection chamber 26. The status sensor 36 is fixed to the base member 35 and is connected to the circuit board 30 in the case 21.

An electric circuit may be formed on a surface of the insulating base member 35 by, for example, printing or etching and may be connected to the stays 33 by, for example, soldering or welding.

The lid-shaped member 27 and the base member 35 are arranged concentrically. As illustrated for example in FIG. 3, two pairs of the detection element 31 and the temperature compensation element 32 are arranged at a predetermined interval on a first circumference which is located at a predetermined first diameter Ra from the center of the base member 35.

The first diameter Ra is smaller than the second diameter Rb. The two pairs of the detection element 31 and the temperature compensation element 32, and the status sensor 36 are arranged on the circumference so as not to coincide with the plurality of (for example, four) gas inlet ports 28 of the lid-shaped member 27 when seen from the axial direction.

Known elements may be employed as the detection elements 31. The detection elements 31 are formed into a substantially ball-shape by covering the surface of a coil of a metal line which contains, for example, platinum having a high temperature coefficient to electric resistance, with a carrier such as alumina which carries a catalyst consisting of, for example, noble metals which are reactive to hydrogen, that is, the detection target gas.

The temperature compensation elements 32 are not reactive to the detection target gas. The temperature compensation elements 32 are formed into a substantially ball-shape by, for example, covering the surface of a coil which is equivalent to the coil of the detection element 31, with a carrier such as alumina.

A difference in electrical resistance value is generated between the detection elements 31 which reach a high temperature by a heat generation due to the combustion reaction generated when hydrogen which is the detection target gas comes into contact with the catalyst of the detection elements 31, and the temperature compensation elements 32 having a temperature lower than that of the detection elements 31 due to no combustion reaction with the detection target gas. The hydrogen concentration can be detected in accordance with the difference and through cancellation of the change in electrical resistance values due to atmospheric temperature.

As illustrated for example in FIG. 2, an explosion-proof filter 41 and a water-repellent filter 42 are provided to cover all of the plurality of gas inlet ports 28, and are arranged in this order from a base end toward a distal end of the gas sensor 1 in the thickness. The explosion-proof filter 41 is an annular shaped mesh or porous sintered filter which is made from, for example, metal or ceramic. The water-repellent filter 42 is an annular shaped filter made from, for example, resin.

An internal cylindrical heater 43 such as a PTC (positive temperature coefficient) thermistor formed from, for example, barium titanate is provided to cover an internal surface 25B of the cylinder member 25. The internal cylindrical heater 43 is in contact with the explosion-proof filter 41 at a radially outside portion (for example, an outer circumferential end of the explosion-proof filter 41) and directly transfers heat to the explosion-proof filter 41.

The PTC thermistor may be employed as the internal cylindrical heater 43. In this case, the Curie temperature can be set to an arbitrary value by arranging the material compositions of the semiconductor ceramic that is mainly formed from barium titanate and forms the PTC thermistor. For example, the internal cylindrical heater 43 can be a constant temperature heater, which utilizes the characteristics in that the electrical resistance suddenly increases when a material is heated above the Curie temperature.

The PTC thermistor generates heat due to the generation of the Joule heat when the voltage is applied onto a PTC element. The resistance value of the PTC element increases logarithmically when the temperature of the PTC element exceeds the Curie temperature. Thus, the current supplied to the PTC element decreases and the increase in the voltage is suppressed. As a result, the heat generating temperature the PTC element decreases. When the resistance value of the PTC element decreases, the current supplied to the PTC element will increase to increase the electrical power again, thereby increasing the heating temperature. By repeating this series of operations, the PTC thermistor works as a constant temperature heater having a self-controlling function.

Accordingly configuration, the inspection target gas introduced from the outside sequentially passes through the water-repellent filter 42 and the explosion-proof filter 41, and is introduced into the gas detection chamber 26. The explosion-proof filter 41 is heated from, for example, the radially outside toward the inside by the heat directly transferred from the internal cylindrical heater 43. Accordingly, the temperature of the inspection target gas is kept higher than the temperature of the dew point, and thus the occurrence of dew condensation in the explosion-proof filter 41 with which the inspection target gas comes into contact can be prevented. At the same time, any moisture adhering to the explosion-proof filter 41 will evaporate.

In accordance with for example the driving state of the fuel cell stack 2, the controller 10 controls operating conditions of the gas sensor 1 and the internal cylindrical heater 43 (for example, each timings of starting and stopping of the operation), and also controls the power supplying status to for example the detection elements 31, the temperature correction elements 32 and the internal cylindrical heater 43.

The controller 10 controls the electrical power supplied to the internal cylindrical heater 43 in accordance with the temperature detected by the status sensor 36. While in an operation or the like of the fuel cell stack 2, the controller 10 controls the temperature and the humidity inside the gas detection chamber 26 detected by the status sensor 36 to be values within the predetermined ranges that suppresses the occurrence of dew condensation.

At this time, the controller 10 controls the amount of electricity supplied to the internal cylindrical heater 43 by, for example, feedback control of the current value supplied to the internal cylindrical heater 43, or by chopper control in accordance with, for example, on/off operations of a switching element (that is, on/off switching control of the electricity supplied to the internal cylindrical heater 43).

The controller 10 independently controls detection of each of the two pairs of the detection elements 31 and the temperature compensation elements 32. A degradation diagnosis is performed to the detection element 31 and the temperature compensation element 32 of each pair through a relative diagnosis or an absolute diagnosis. In the relative diagnosis, detection values obtained for each pair are compared to each other. In the absolute diagnosis, the detection values obtained for each pair are independently compared with a predetermined reference value. With the result of the diagnosis, concentration of hydrogen which is the detection target gas is calculated by referring to, for example, a predetermined map of hydrogen concentration in accordance with the detection values obtained from either one of the two pairs of the detection elements 31 and the temperature compensation elements 32.

As described above, in the gas sensor 1 according to the present embodiment, the gas inlet ports 28 which allow the introduction of the inspection target gas from the outside into the gas detection chamber 26 are arranged on the circumference so as not coinciding with the status sensor 36, the plurality of the detection elements 31 and the plurality of the temperature compensation elements 32 in the gas detection chamber 26 when seen from the axial direction. Accordingly, the status sensor 36, the plurality of the detection elements 31 and the plurality of the temperature compensation elements 32 are arranged at locations off a path through which the inspection target gas flows. It is therefore possible to prevent the inspection target gas from being blown directly against the status sensor 36, the plurality of the detection elements 31 and the temperature compensation elements 32. Accordingly, even if the inspection target gas has a high moisture content and a high humidity, the occurrence of dew condensation in the status sensor 36, the plurality of the detection elements 31 and the temperature compensation elements 32 can be prevented.

Since the status sensor 36 is disposed at the substantially central portion of the base member 35, accuracy and reliability in detection of the temperature and the humidity within the gas detection chamber 26 can be improved.

The two pairs of the detection element 31 and the temperature compensation element 32 are arranged on a first circumference at a predetermined interval in the circumferential direction. The first circumference has a first diameter Ra which is smaller than the second diameter Rb of the second circumference on which the plurality of (for example, four) gas inlet ports 28 are arranged. Accordingly, the plurality of the detection elements 31 and the temperature compensation elements 32 can be arranged more densely, and the size of the gas sensor 1 can be reduced.

Since all of the plurality of the gas inlet ports 28 arranged on the second circumference can be covered with a single annular water-repellent filter 42, it is possible to keep the water-repellent filter 42 simply-structured and compact, and to prevent an increase in number of the water-repellent filter 42.

A structure in which the internal cylindrical heater 43 and the explosion-proof filter 41 are in direct contact with each other is employed as s heat-transfer structure to transfer heat generated by the internal cylindrical heater 43 to the explosion-proof filter 41. Accordingly, the explosion-proof filter 41 can be efficiently heated by the heat transferred from the internal cylindrical heater 43 and clogging of the explosion-proof filter 41 due to dew condensation can be prevented.

All of the plurality of the inlet ports 28 arranged on the second circumference can be covered with a single annular explosion-proof filter 41. It is therefore possible to keep the explosion-proof filter 41 simply-structured and compact, and to prevent an increase in number of the explosion-proof filter 41. Since the explosion-proof filter 41 comes into direct contact with the internal cylindrical heater 43 at the radially outside portion, the heat generated by the internal cylindrical heater 43 is transferred from the radially outside with a relatively large heat release area toward the inside with a relatively small heat release area in the annular explosion-proof filter 41. Accordingly, the explosion-proof filter 41 can be heated efficiently and the temperature of the inspection target gas which passes through the explosion-proof filter 41 can be held at a temperature higher than the dew point. Thus, the occurrence of dew condensation in the explosion-proof filter 41 with which the inspection target gas comes into contact can be prevented. Any moisture adhering to the explosion-proof filter 41 will evaporate easily.

In the present embodiment, the gas sensor 1 is a gas-contact combustion-type sensor. However, the present invention is not limited to this configuration, and other types of sensors may be used such as a semiconductor type sensor that detects the gas concentration in accordance with an element resistance value that is produced when the detection target gas comes into contact with and depart from oxygen on a surface of the detection element.

In the present embodiment, the cylinder member 25 and the lid-shaped member 27 are made from a ceramic material. However, the present invention is not limited to this configuration, and the cylinder member 25 and the lid-shaped member 27 may be made from, for example, metal or resin.

In the present embodiment, the internal cylindrical heater 43 is a PTC thermistor. However, the present invention is not limited to this configuration, and other heaters such as a sintered heater, or a heater that is formed by printing and sintering a conductive resistor on the internal surface 25B of the cylindrical member 25 to form a conductive pattern of a part of the electric circuit, may be employed.

Figure 4:
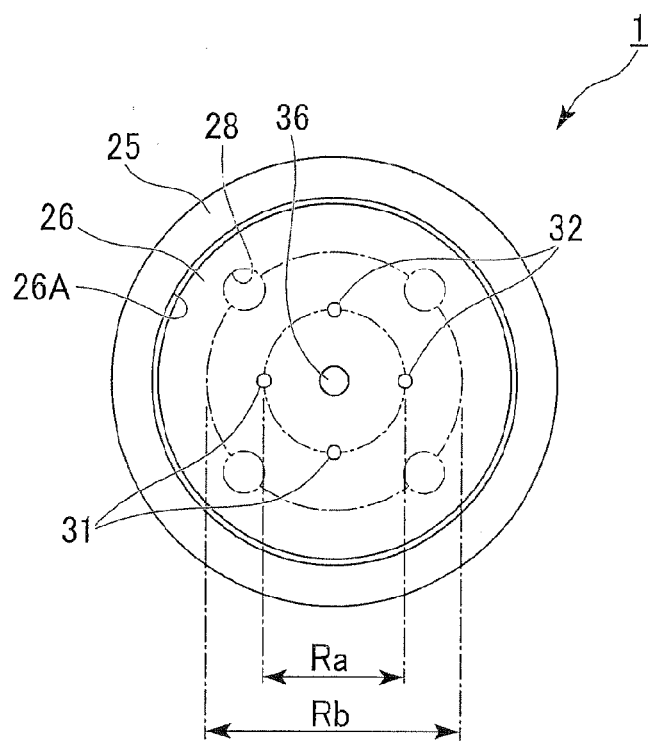
FIG. 4 is an axial sectional view of a gas sensor according to a variant example of one embodiment of the present invention.
Figure 5:
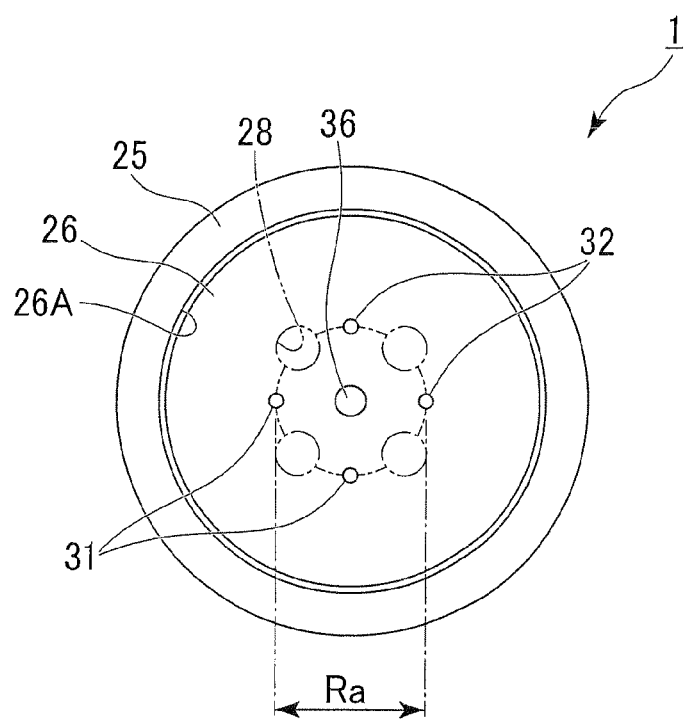
FIG. 5 is an axial sectional view of a gas sensor according to a variant example of one embodiment of the present invention.

In the embodiment described above, as illustrated for example in FIG. 4, the plurality of the detection elements 31 and the temperature compensation elements 32 arranged on the first circumference and the plurality of the gas inlet ports 28 arranged on the second circumference may be positioned in different phases. That is, as illustrated for example in FIG. 5, the plurality of the detection elements 31, the temperature compensation elements 32 and the plurality of the gas inlet ports 28 may be arranged on the same circumference (for example, on the first circumference). In this case, the plurality of the detection elements 31, the temperature compensation elements 32 and the plurality of the gas inlet ports 28 can be arranged more densely to further reduce the size of the gas sensor 1.

Figure 6:
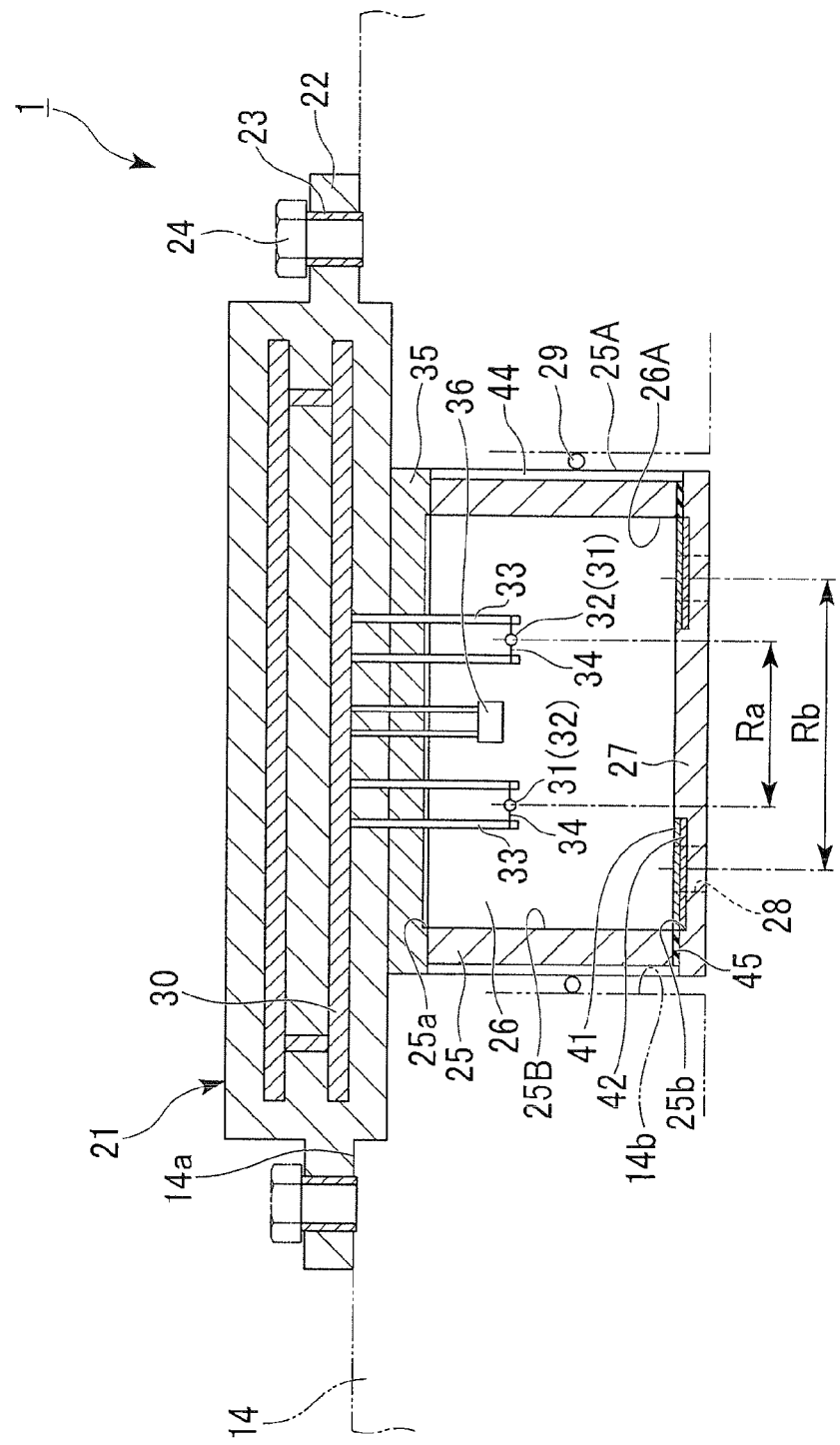
FIG. 6 is a side sectional view of a gas sensor according to a variant example of one embodiment of the present invention.

The embodiment described above is provided with the internal cylindrical heater 43. However, the present invention is not limited to this configuration, and, for example, instead of the internal cylindrical heater 43, an external cylindrical heater 44, such as a PTC (positive temperature coefficient) thermistor formed from, for example, barium titanate may be provided to cover the external surface 25A of the cylinder member 25. In this case, as illustrated for example in FIG. 6, the external cylindrical heater 44 is connected to the explosion-proof filter 41 at a radially outside portion (for example, an outer circumferential end of the explosion-proof filter 41) by a heat-transfer member 45 which penetrates the cylinder member 25 and is formed from a highly heat conductive material. Accordingly, the heat generated by the external cylindrical heater 44 can be transmitted indirectly to the explosion-proof filter 41.

Figure 7:
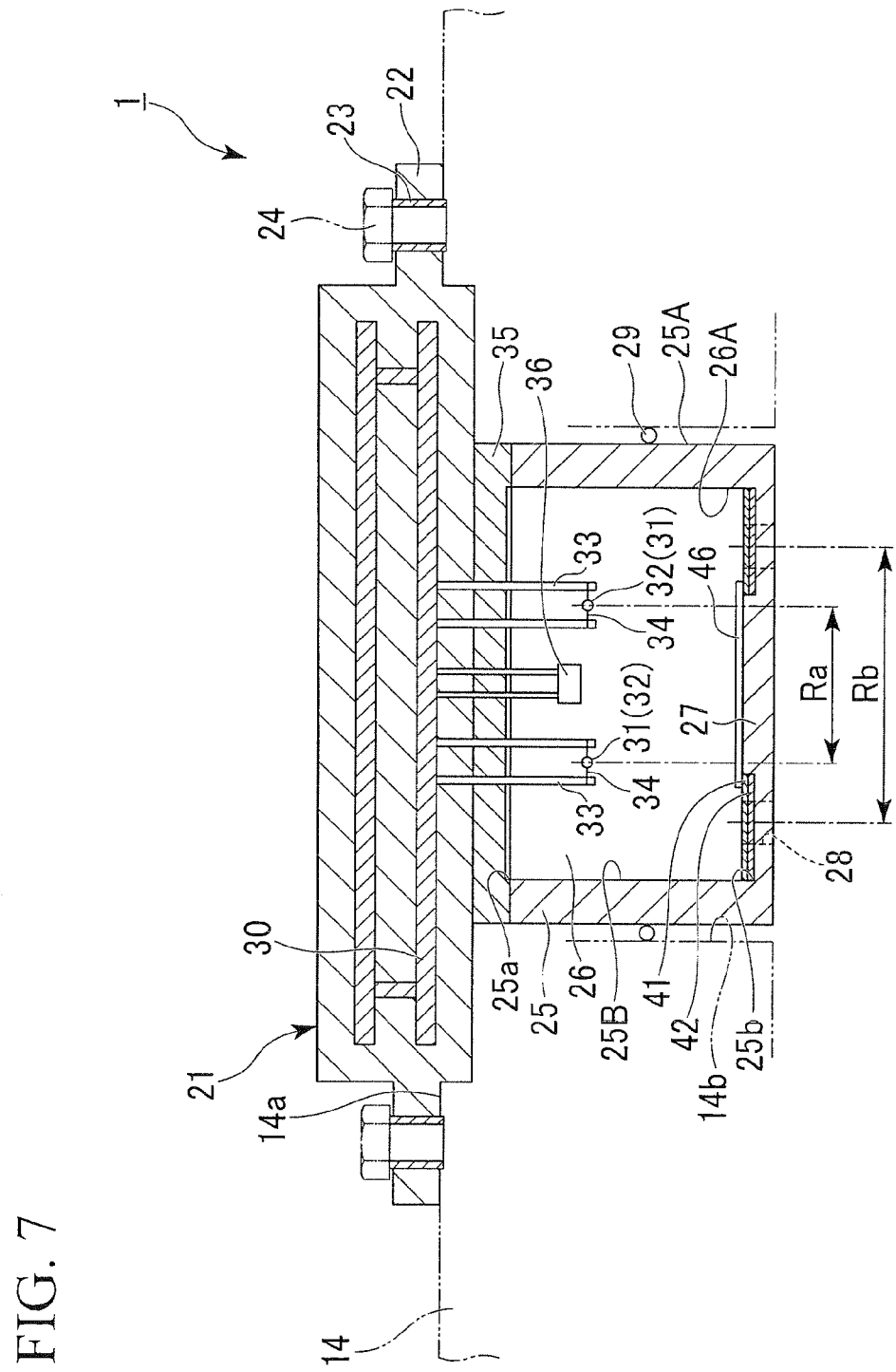
FIG. 7 is a side sectional view of a gas sensor according to a variant example of one embodiment of the present invention.

In addition, as illustrated for example in FIG. 7, a plate-shaped heater 46, such as a PTC (positive temperature coefficient) thermistor formed from, for example, barium titanate may be provided in contact with a radially inside portion of the explosion-proof filter 41 instead of the internal cylindrical heater 43.

In the embodiment described above, the explosion-proof filter 41 and the water-repellent filter 42 have annular shapes. However, the present invention is not limited to this configuration, and, for example, at least one of the explosion-proof filter 41 and the water-repellent filter 42 may have a disc shape.

The embodiment described above is provided with the explosion-proof filter 41 and the water-repellent filter 42 which cover the gas inlet port 28. However, the present invention is not limited to this configuration, and, for example, at least one of the explosion-proof filter 41 and the water-repellent filter 42 may be omitted.

The embodiment described above is provided with the internal cylindrical heater 43. However, the present invention is not limited to this configuration, and the internal cylindrical heater 43 may be omitted.

Figure 8:
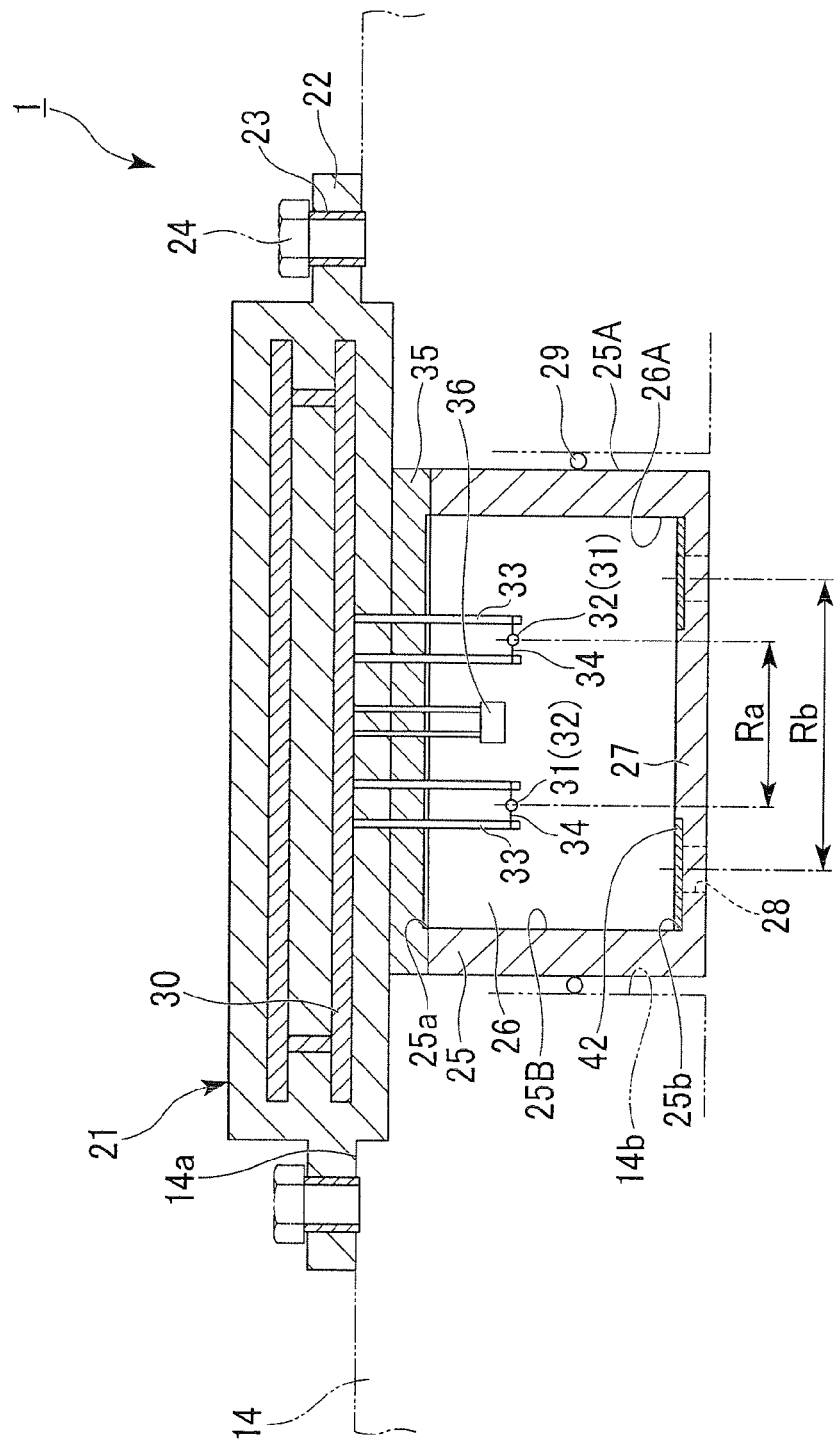
FIG. 8 is a side sectional view of a gas sensor according to a variant example of one embodiment of the present invention.

For example, as illustrated in FIG. 8, in the gas sensor 1 related to a variant example of the embodiment described above, both the internal cylindrical heater 43 and the explosion-proof filter 41 are omitted.

In the embodiment described above, the explosion-proof filter 41 and the water-repellent filter 42 are arranged in this order from the base end toward the distal end of the gas sensor along the thickness direction of the gas sensor 1. However, the present invention is not limited to this configuration, and the explosion-proof filter 41 and positions of the water-repellent filter 42 may be interchanged.

INDUSTRIAL APPLICABILITY

With the gas sensor according to the present invention, it is possible to prevent the flow of the inspection target gas from being directly blown onto the status sensor and the gas detection elements. Accordingly, even if the inspection target gas has a high moisture content and a high humidity, the occurrence of dew condensation in the status sensor and the gas detection elements can be prevented. Since the status sensor is disposed at the substantially central portion of the base member, accuracy and reliability in detection of the temperature or the humidity within the gas detection chamber can be improved.

REFERENCE NUMERALS

1: gas sensor
25: cylinder member (cylindrical-shaped member)
25a and 25b: openings 26: gas detection chamber
27: lid-shaped member
28: gas inlet port
31: detection element (gas detection element)
32: temperature compensation element (gas detection element)
35: base member
36: status sensor
41: explosion-proof filter
42: water-repellent filter
43: internal cylindrical heater (heater)
44: external cylindrical heater (heater)
45: heat-transfer member (heat-transfer structure)
46: plate-shaped heater (heater)

The invention claimed is:

1. A gas sensor, comprising:
a cylindrical member which includes a gas detection chamber therein and extends along an axis thereof;
a base member which closes an opening of a first axial end of the cylindrical member;
a status sensor which is disposed at a substantially central portion of the base member, and detects at least the temperature or the humidity in the gas detection chamber;
a plurality of gas detection elements disposed around the status sensor on the base member;
a lid member which closes an opening of a second axial end of the cylindrical member; and
a plurality of gas inlet ports which penetrates the lid member and enables the introduction of an inspection target gas from an outside into the gas detection chamber,
wherein all of the plurality of gas inlet ports are arranged at locations not coinciding with the status sensor and the gas detection element when viewed from the axial direction,
the plurality of the gas detection elements are arranged on a first circumference;
the plurality of the gas inlet ports are arranged on the first circumference or on a second circumference of a different diameter from that of the first circumference; and
the plurality of the gas detection elements arranged on the first circumference and the plurality of the gas inlet ports arranged on the first circumference or the second circumference are positioned in different phases along the circumferential direction.

2. The gas sensor according to claim 1, wherein:
the plurality of the gas inlet ports are arranged on the second circumference of a larger diameter than that of the first circumference.

3. The gas sensor according to claim 2, further comprising an annular water-repellent filter which covers all the plurality of the gas inlet ports arranged on the second circumference.

4. The gas sensor according to claim 2, further comprising:
a heater disposed on a wall of the cylindrical member or on the lid member to heat the inside of the gas detection chamber; and
an explosion-proof filter which covers the plurality of the gas inlet ports, and is made from metal,
wherein a heat-transfer structure is provided which transfers heat generated by the heater to the explosion-proof filter.

5. The gas sensor according to claim 4, wherein:
the heater is disposed on the wall of the cylindrical member;
the explosion-proof filter has an annular shape to cover all the plurality of the gas inlet ports arranged on the second circumference; and
the heat-transfer structure transfers heat generated by the heater from radially outside toward the inside of the explosion-proof filter.

6. The gas sensor according to claim 2, wherein:
the first circumference has a first diameter from a center of the base member; and
the second circumference has a second diameter from the center of the base member.

* * * * *